United States Patent
Marra et al.

(10) Patent No.: US 11,861,920 B2
(45) Date of Patent: Jan. 2, 2024

(54) SYSTEM FOR MONITORING GLUTEN CONSUMPTION AND PREDICTING ASSOCIATION OF INDISPOSITION TO GLUTEN CONSUMPTION

(71) Applicants: SOCIEDADE BENEFICENTE ISRAELITA BRASILEIRA HOSPITAL ALBERT EINSTEIN, São Paulo (BR); I-HEALTHSYS PRODUTOS MÉDICOS LTDA-ME, São Carlos (BR)

(72) Inventors: Alexandre Rodrigues Marra, São Paulo (BR); Marcelo Prado, São Carlos (BR); Renaldo Massini Junior, São Carlos (BR); Silvia Maria Prado, São Carlos (BR)

(73) Assignees: SOCIEDADE BENEFICENTE ISRAELITA BRASILEIRA HOSPITAL ALBERT EINSTEIN, São Paulo (BR); I-HEALTHSYS PRODUTOS MÉDICOS LTDA-ME, São Carlos (BR)

(*) Notice: Subject to any disclaimer, the term of this patent is extended or adjusted under 35 U.S.C. 154(b) by 87 days.

(21) Appl. No.: 17/571,979

(22) Filed: Jan. 10, 2022

(65) Prior Publication Data
US 2022/0415065 A1    Dec. 29, 2022

(30) Foreign Application Priority Data
Jun. 28, 2021   (BR) .................. 10 2021 0128410

(51) Int. Cl.
*G06T 7/70*    (2017.01)
*G06V 20/68*    (2022.01)
*G06V 10/84*    (2022.01)
*G06V 10/10*    (2022.01)

(52) U.S. Cl.
CPC ............... *G06V 20/68* (2022.01); *G06T 7/70* (2017.01); *G06V 10/19* (2022.01); *G06V 10/84* (2022.01); *G06T 2207/20076* (2013.01); *G06T 2207/30128* (2013.01)

(58) Field of Classification Search
CPC ........ G06V 10/84; G06V 10/19; G06V 20/68; G06T 2207/20076; G06T 2207/30128; G06T 7/70; G16H 50/30; G16H 50/20; G16H 20/60
See application file for complete search history.

(56) References Cited

U.S. PATENT DOCUMENTS

| | | | | |
|---|---|---|---|---|
| 2014/0178903 | A1* | 6/2014 | Sousa Martin | G01N 33/5308 435/7.92 |
| 2014/0315162 | A1* | 10/2014 | Ehrenkranz | G01G 19/4146 434/127 |
| 2018/0144821 | A1* | 5/2018 | Irani-Cohen | G16H 20/60 |
| 2018/0317530 | A1* | 11/2018 | Rade-Kukic | A23L 7/11 |
| 2019/0080629 | A1* | 3/2019 | Gopalan | G16H 40/63 |

* cited by examiner

*Primary Examiner* — Syed Haider
(74) *Attorney, Agent, or Firm* — B. Aaron Schulman, Esq.; Stites & Harbison, PLLC

(57) ABSTRACT

A system for monitoring gluten consumption, especially in celiac people, which allows the feeding of food consumption data and updating, in real time, of the estimated amount of gluten consumed daily. Still, the present invention refers to a system for prediction that associates the possibility of an indisposition being associated or not with an undue consumption of gluten.

2 Claims, 2 Drawing Sheets

SYSTEM FOR MONITORING GLUTEN CONSUMPTION AND PREDICTING ASSOCIATION OF INDISPOSITION TO GLUTEN CONSUMPTION

FIELD OF THE INVENTION

The present invention refers to a system for monitoring gluten consumption, especially of people with celiac disease, as well as a prediction system that associates the possibility of a physical indisposition being associated or not with a consumption above of a certain maximum daily limit of gluten.

STATE OF THE ART

The celiac disease affects about three percent of the world's population and is basically caused by an immune system reaction of a subject, which can trigger an inflammatory process of the small intestine. In more severe cases, celiac disease can lead to clinical presentations of lymphoma or tumors.

Patients with celiac disease need to control their diet and the type of food consumed to avoid triggering an immune system reaction. For this, patients with celiac disease should preferably consume gluten-free foods. Natural foods such as fruits, vegetables and milk are gluten-free. Normally processed foods have gluten in their composition, due to the industrialization process itself.

In this context, several solutions developed to help patients with celiac disease to identify amounts of gluten in different foods and control their consumption are known from the state of the art.

As examples of such developments, document U.S. Pat. No. 10,528,793 B2 can be cited, which describes a method of food identification that comprises identifying, from an image, different foods on a plate and indicating a risk classification for each food identified. The identification of the image and the associated risk can occur through artificial intelligence, using databases with information about the allergen.

Document U.S. Pat. No. 9,442,100 describes a system for measuring calorie consumption that combines image analysis and a spectroscopy sensor. The system can also measure specific nutrients or ingredients, including allergens. The system can also take into account information about the location/establishment where the image was captured.

Document U.S. Pat. No. 9,977,980 discloses a method of identifying the nutritional content of a food from the analysis of an image of the meal. The method uses artificial intelligence with training models that can take into account the location or establishment where the image was captured.

The document U.S. Pat. No. 9,734,426 describes a method of identifying the nutritional content of a food from the analysis of an image of the meal. The method uses artificial intelligence with training models that can take into account user feedback, information about the location/establishment where the image was captured and the user's consumption history.

Although there is a vast amount of state of the art documents referring to the same technological field, the state of the art lacks, for example, a solution that specifies the ability to reach an accuracy in the detection of gluten at low concentrations, a probability calculation of risk associated with excessive gluten consumption, such probability calculation of risk being able to be of association.

Thus, the state of the art does not provide an effective tool to help a person with celiac disease to balance the amount of gluten ingested. The existing technologies are standalone technologies, which either measure or predict the amount of gluten in the food being eaten or do antibody tests to check whether or not the person has consumed gluten and has had an immune system reaction.

SUMMARY OF THE INVENTION

It is one of the objectives of the present invention to provide a system for monitoring gluten consumption based on foods consumed by an individual.

It is also an objective of the present invention to provide a system for monitoring gluten consumption comprising several sources for capturing information about the amount of gluten in food.

It is one more of the objectives of the present invention to provide a system for monitoring gluten consumption capable of identifying and quantifying low concentrations of gluten in foods, in order to provide a system of high sensitivity and specificity.

Another objective of the present invention is to provide a system for monitoring gluten consumption capable of monitoring and storing history of gluten consumption.

Another objective of the present invention is to provide a system capable of storing a history of the physical symptoms experienced by the patient that may be related to the symptoms of celiac disease.

It is also an objective of the present invention to provide a system for predicting the association of indisposition in an individual to inadequate gluten consumption, so that the system provides a probabilistic result on whether a certain indisposition is or is not due to inadequate consumption or above a certain pre-set gluten limit, based on monitoring data of an individual's gluten consumption.

The present invention refers to a system for monitoring gluten consumption, which comprises a device configured to capture information related to the consumption of a food, such information allowing the identification, estimation and/or association of the gluten content of the food; the device being further configured to receive, via an input interface, information on an individual's food consumption; a database that receives and stores information related to food consumption and information about the individual's food consumption, the database also storing a maximum limit for the consumption of gluten allowed for the individual; a processor with analysis software embedded in its internal memory or stored on an Internet server with access by the processor, to estimate a daily amount of gluten consumed by the individual, during a predetermined period of time, for example, and not limited to, twenty-four hours to carry out a probabilistic analysis based on the information stored in the database; wherein the estimate of the daily amount of gluten consumed by the individual is updated, in real time, at each new receipt of information related to food consumption and/or information on the individual's food consumption; and wherein a warning is generated to the individual when the processor estimates that the next consumption of food will exceed the pre-set daily limit of consumption of gluten admitted for the individual.

Information on food consumption includes type of food, its respective quantity, time and place of consumption. The probabilistic analysis to determine the amount of daily gluten consumed is performed by summing the probability that each food has gluten in its composition, given by the product between the estimated amount of food eaten and the total amount of estimated gluten consumed associated with each food.

Still, the present invention relates to a system for predicting the association of indisposition to gluten consumption, which comprises a device configured to capture information related to the consumption of a food, such information allowing the identification, estimation and/or association of the gluten content of the food; the device being further configured to receive, via an input interface, information on an individual's food consumption; a database that receives and stores information related to food consumption and information about the individual's food consumption, the database also storing a maximum limit for the consumption of gluten allowed for the individual; a processor to estimate a daily amount of gluten consumed by the individual from a probabilistic analysis based on information stored in the database, forming a history of daily gluten consumption per individual; wherein an individual, when informing the device, through its interface, about a physical indisposition, causes the system to carry out a step of evaluation and calculation of the probability of the cause of the indisposition, in order to predict, by a percentage numerical result, if such indisposition is a result of the immune system's reaction to gluten.

The step of evaluating and calculating the probability of the cause of the indisposition is performed by estimating the gluten consumption by the patient in the last twenty four hours, or another pre-defined time interval, and the probability of the patient having symptoms of celiac disease as a function of the amount of gluten consumed. This calculation is performed through an initial estimate of probability as a function of gluten consumption using a Poisson-type probability function distribution.

In addition, the system tracks the consumption of gluten most likely to be the cause of indisposition, by evaluating the history of stored consumption data and the physical symptoms presented by the patient.

BRIEF DESCRIPTION OF THE FIGURES

The present invention will be further explained based on the figures specified below.

DETAILED DESCRIPTION OF THE INVENTION

Figure 1:
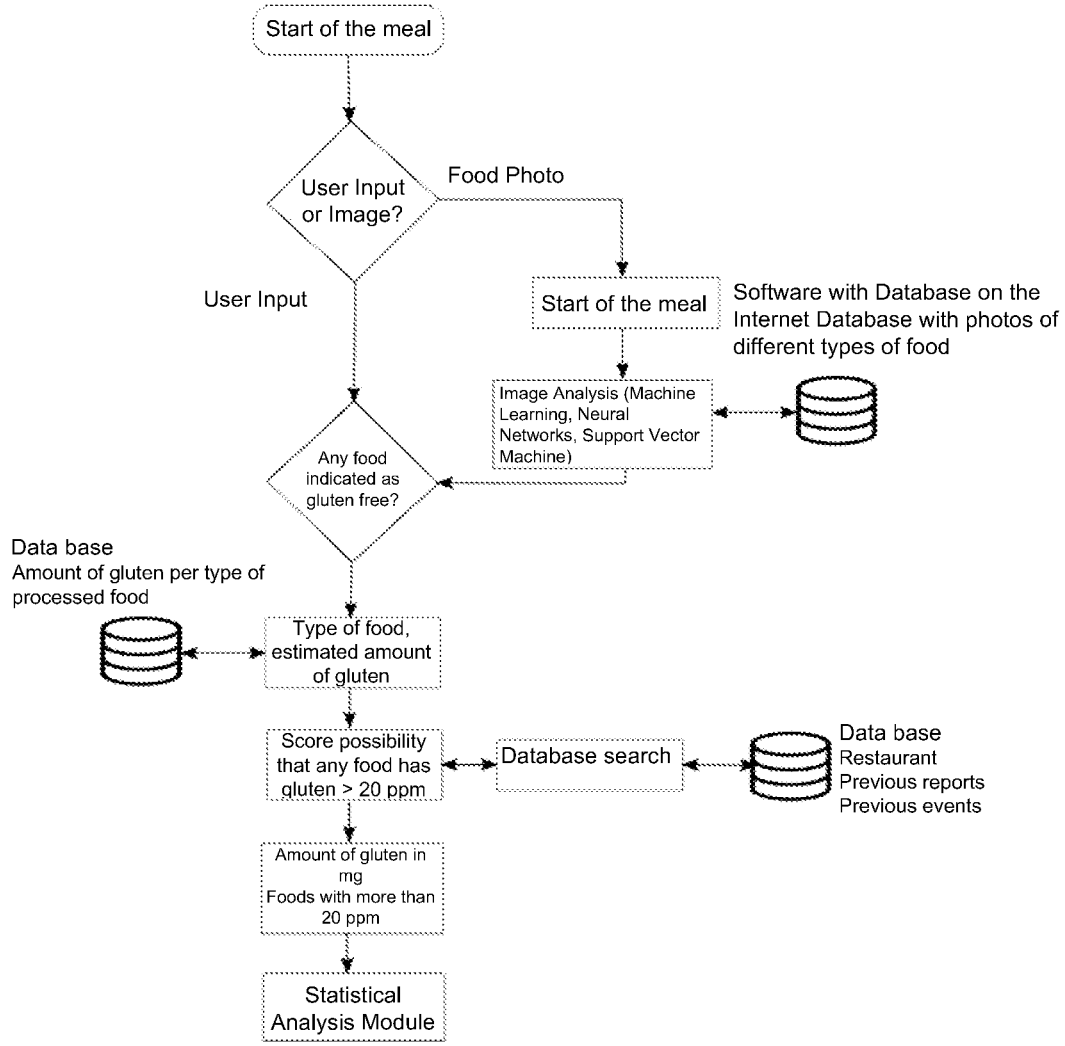
FIG. 1 illustrates the flowchart that represents the insertion of food information, at the beginning of a meal, in the device of the system for monitoring gluten consumption according to the present invention.

In many countries, processed foods that are said to be gluten free may actually contain a small amount of gluten, and a maximum amount of gluten must be adhered to before they can be sold as "gluten free". In Brazil, for a processed food to be sold as "gluten free", it must have a maximum of 20 parts per million (ppm) of gluten.

People with celiac disease need to control the consumption of processed foods to avoid the immune system reaction, but even consuming "gluten-free" products, they end up ingesting amounts of gluten which, although minimal, can become significant when considering the effect of cumulative consumptions.

Thus, when consuming "gluten-free" processed foods, the individual needs to pay attention to the amount of processed foods consumed in order not to consume the maximum amount of gluten indicated for the patient with celiac disease, which is up to 10 mg of daily gluten in processed foods.

For example, if an individual were to consume 300 g of a food known as "gluten free" comprising in its composition a value of 20 ppm of gluten, approximately 6 mg of gluten would be consumed. Thus, if this same food has 50 ppm, when consuming 300 g, the individual would be ingesting 15 mg of gluten, that is, 5 mg above the recommended maximum, and may, therefore, present a clinical condition of inflammation of the small intestine and others symptoms associated with celiac disease.

Controlling the food consumed daily by individuals with celiac disease is quite laborious, and it is necessary to control and balance the food in order not to exceed a maximum of 10 mg of gluten daily.

In case the individual has consumed more than 10 mg of gluten and is sick due to the immune system reaction, he will have to assess which food and, in case he ate outside home, where that food was consumed. However, the immune response may take a few days, thus making it difficult to identify the cause of the occurrence of such indisposition/inflammation.

Furthermore, another problem that celiac individuals face is the frequent uncertainty about whether an indisposition is associated with gluten consumption. This is because many of the symptoms of a patient with celiac disease are similar to other common illnesses, such as: diarrhea, malaise, headache, stomachache, and there may be confusion about the exact cause of the indisposition. Thus, rapid antibody tests are used in order to be sure that gluten consumption is the cause of the indisposition.

There are some solutions on the market that test foods for gluten in their composition. These equipments use some technologies based on reagents, which change color in contact with gluten-containing foods, or through mass spectroscopy technology, measuring the components present in foods.

Another technology for detecting the amount of gluten in food is image analysis, which, through artificial intelligence techniques, performs the analysis of food and makes a prediction of the amount of gluten and calories it may have.

Thus, the present invention provides an effective solution for individuals with celiac disease to monitor the food they are consuming and balance their gluten consumption. As avoiding eating completely gluten-free food is practically impossible, a methodology that can be applied in a device with software to help the celiac individual to monitor such consumption is extremely necessary.

The system of the present invention comprises, for data acquisition and information processing, a device configured to capture information related to the consumption of a food, such information allowing the identification, estimation and/or association of the gluten content of the food. The device is also configured to receive, through an input interface, information about an individual's food consumption.

The device of the system according to the present invention is provided with a set of sensors, so that the device performs data acquisition and information processing and can, when available, be fed with data from the gluten sensors. The system can also be fed with data from antibody tests that are carried out for the individual. The detection of gluten and its quantities can also be performed, in addition to artificial intelligence techniques applied to image recognition, by any technologies of the spectrometry type, or even with the use of chemical reagents.

In this way, the device of the system of the present invention works as a data repository, so that an individual makes records of meals (food, quantities, days and places), which are stored in the system to constitute the database, which it is continuously fed.

Such data start to compose a database that receives and stores information related to food consumption and information on the individual's food consumption, the database also storing a maximum limit for the consumption of gluten admitted for the individual.

Thus, it is possible, for example, that a screening is made about the food and the place where it was consumed, which may have provoked this immune system reaction due to having a high amount of gluten.

The device with interface and the set of sensors for data acquisition and information processing system according to the present invention comprises a set of detection sensors to identify quantities of gluten in food, which may be part of the device itself or attached to it, for example: sensors for the detection of gluten, such as chemical sensors or by spectrometry.

The device interface is any interface capable of performing information input by an individual. The set of sensors comprises at least one barcode reader, for obtaining data from industrialized food labels, as well as photo sensors, capable of, through images, identifying consumed foods, as well as their quantities, and measuring the amount of gluten involved by associating such foods and amounts with data from the system's database according to the present invention.

In the case of capturing information, through artificial intelligence techniques (Machine Learning, Neural Networks, Support Vector Machine), a cloud software with Internet access performs the analysis of the food, accessing a previously available database with dozens of thousands of photos of food in different types of combinations and dishes. This database can be continuously updated, so that several other types of food can be detected (for example, if the artificial intelligence algorithm does not correctly detect the food, the user manually enters the data, and from that moment onwards the database will be updated).

However, by comprising a set of sensors (as part of the sensor or attached to it), the device of the system according to the present invention makes an assessment of the amount consumed far beyond the bar code reading alone. Thus, based on the data obtained by the set of sensors of the system according to the present invention, an estimate of gluten consumption is carried out using statistical analysis.

Thus, through the interface for data acquisition and information processing, data that form a database about food and its gluten content are inserted. Once the food and its consumed quantities are inserted into the device, a probabilistic analysis is performed taking into account each food consumed, so that, in a state of indisposition of the individual, a probability that such an indisposition is or is not the result of an immune system reaction is calculated. The data is of course processed by a software on the processor which is included in the device of the system of the present invention or in a software on the Internet that the processor has access to.

In this sense, as illustrated in FIG. 1, which represents a flowchart of information insertion in the device of the system according to the present invention, at the beginning of a meal, in which the data can be inserted manually, or even by images, by the user through an application/software on mobile devices. Another option is for the user to take a picture of the food on the plate and the device automatically identify, through the software, the consumed foods and their respective quantities. As shown in FIG. 1, after this step of detecting the types of food in the meal, a software will carry out the analysis to estimate the amount of food and gluten in each food in the meal, taking into account a database with the amount of gluten in each food available in a library, whether online or offline. This database will always be updated to include new types of food with or without gluten.

Also, as shown in the flowchart in FIG. 1, it is necessary to inform if any of the foods being consumed is considered to be gluten-free, that is, with less than 20 ppm in its composition. This information can also be read using the barcode reader or QR code on the product packaging. A database of registered gluten free food labels will be made available to check if this product is registered and if it is really gluten free. If the product is not registered, this information will be sent to an external support team for checking and obtaining information.

The system of the present invention can also, through sensors and identification means, identify the presence of gluten in foods, even those that are natural, which may include traces of gluten, arising, for example, from cross contamination.

Thus, all the information acquired will be to estimate the amount of daily gluten consumption of an individual and also for a probabilistic analysis and consequent statistical prediction about whether an individual's indisposition is associated with gluten consumption or not.

Figure 2:
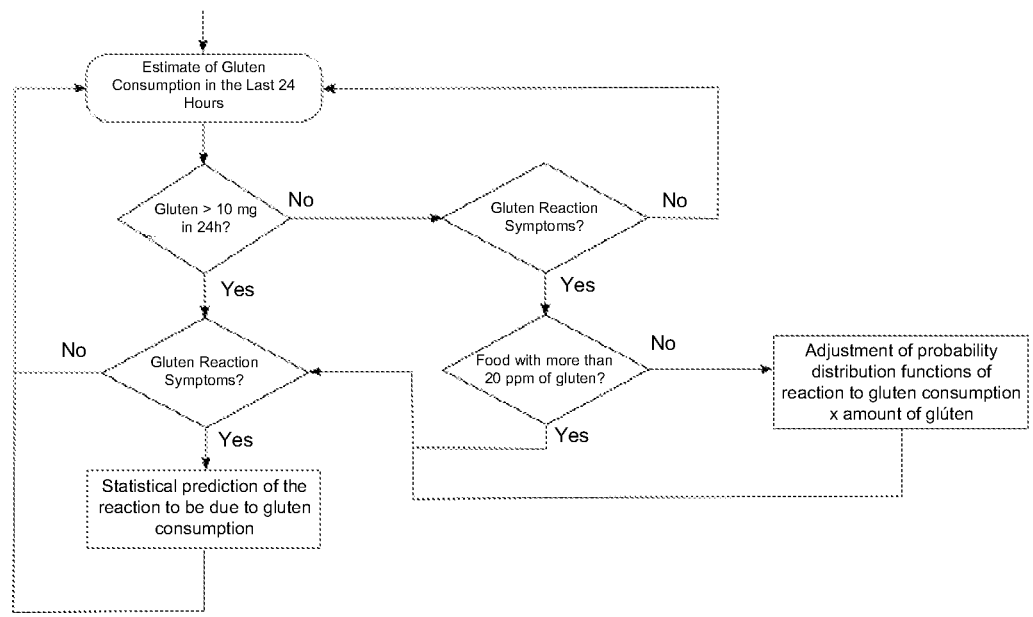
FIG. 2 illustrates the flowchart that schematically represents the statistical prediction of the amount of gluten consumption ingested by an individual.

Thus, FIG. 2 represents a flowchart for the statistical prediction of the amount of ingested gluten consumption, the determination of the accumulated gluten consumption of processed foods called gluten free (that is, comprising an amount of gluten less than 20 ppm) during a pre-determined amount of time, for example in the last 24 hours, to have exceeded a maximum quantity of gluten that is safe for celiac patients and the estimate of if any food consumed has a value equal to or greater than 20 ppm in its composition (maximum limit established).

Typical celiac disease reaction symptoms will be monitored 24 hours a day and a statistical prediction will be performed to check the likelihood of these reactions in the individual's body being due to gluten consumption above what is allowed for a person with celiac disease.

For the statistical estimation of gluten consumption and prediction of possible side effects due to gluten consumption, a Poisson distribution probability analysis is performed, according to equation 1, which is a probability distribution for random variable that expresses the probability of a series of events occurring in a certain period of time if these events occur regardless of when the last event occurred.

In equation (1), which makes it possible to estimate the probability of occurrence of a given event x, $\lambda$ is the average of events over a period of time or the average rate of occurrence per measured unit; the random variable X being the count of the number of events occurring in the interval.

$$\mathbb{P}(X=x) = e^{-\lambda}\frac{\lambda^x}{x!} \quad x = 0, 1, 2, 3 \ldots \quad \text{(Equation 1)}$$

Thus, in real time, the system according to the present invention updates the amount of daily gluten consumed by the individual and makes this estimate available continuously. In the case of a meal in which a "gluten-free" processed food is consumed (thus having a gluten amount of less than 20 ppm), which, cumulatively, can generate an autoimmune response due to gluten consumption, the system generates warnings to the user (through a notification, such as: sound, visual or message alert on mobile device) that the food to be consumed may generate the said autoimmune response due to the consumption of gluten.

Figure 3:
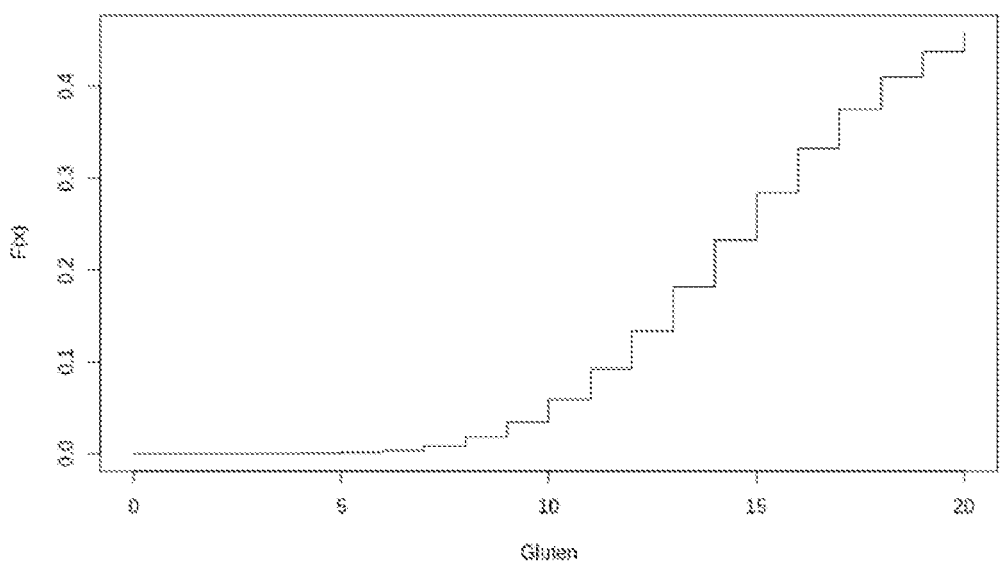
FIG. 3 represents a graph of the accumulated probability function as a function of the amount of gluten ingested by an individual.

The 24-hour cumulative Poisson distribution function, for example, of gluten consumption initially to be used for the probability calculation can be seen in FIG. 3. This function is adjusted over time, according to the number of times the symptoms will be experienced by the patient and according to the antibody tests that the patient will perform. To adjust this curve, neural network or error minimization techniques can be used (least squares method, for example).

In any case, a celiac individual may eventually exceed this amount or not and still have an indisposition. Thus, the present invention also relates to a prediction system for the association of indisposition in an individual to inadequate gluten consumption.

In this sense, if a celiac individual experiences an indisposition, with symptoms such as diarrhea, vomiting, headache, fever, malaise, the data and information processing system is activated to carry out a step of evaluation and calculation of the probability of the cause of the indisposition, in order to predict whether the indisposition is a result of the immune system's reaction to gluten.

In FIG. 3, the gluten accumulated density function in the last 24 hours is shown. From 10 mg of gluten consumption, the probability of the patient to present symptoms increases more rapidly. This accumulated probability function graph will be readjusted over time according to the data collected from the patient. The curve can be adjusted and a new estimated curve obtained after adjustment processes using, for example, least squares techniques, neural networks, support vector machine or another artificial intelligence technique.

As an example of the case of accumulated gluten consumption in the last 24 hours, given a Poisson distribution with rate $\lambda=15$, with the probability distribution as a function of gluten consumption shown in FIG. 3. The table below shows the minimum quantity of gluten $Q_{min}$ in milligrams and the minimum probability $P_{min}$ of the patient having symptoms and the maximum quantity of gluten $Q_{max}$ in milligrams and the maximum probability $P_{max}$ of the patient having symptoms for this Poisson distribution.

| $\lambda$ | $Q_{min}$ (mg), $P_{min}$ | $Q_{max}$ (mg), $P_{max}$ |
|---|---|---|
| 15 | 12; 0.29 | 20; 0.62 |

The examples above demonstrate the calculation of the probability that the patient will develop an immune system response given a particular Poisson distribution with $\lambda=15$. This is just an example, and the algorithm can define other values of $\lambda$ depending on the patient's history of symptoms and the antibody tests to be performed, in such a way as to obtain a Poisson distribution of probability that is the most suitable for a given patient.

With the symptom data to be provided, the likelihood of the gluten reaction can be validated. A temporal follow-up regarding the amount of accumulated gluten should be carried out and adjustments over time can refine the process so that the system's response in relation to the reactions of the immune system due to the consumption of gluten by the patient with celiac disease is increasingly accurate.

A particular case, which can happen a few times, is the patient having an antibody test for celiac disease. If the antibody test gives a positive result for that amount of gluten that was estimated by the system, it will be extra data to help correct the Poisson distribution curves. However, as it is not possible to be sure that the amount of gluten consumed estimated by the system was completely correct, these adjustments to the Poisson distribution with the antibody tests will only be performed after a certain minimum sampling of antibody tests, so that the sampling is statistically significant. For example, with the antibody test the curve can be readjusted every 10 tests performed. This is just an example, you can use more or less tests to correct the curve via definition of this parameter in the system software.

By storing data in the database and over time, the system will store more data relating to health status and antibody tests performed, and with the present invention it will tend to be more accurate in diagnosing and alerting the individual with celiac disease.

Having described an example of preferred embodiment of the present invention, it should be understood that the scope of the present invention encompasses other possible variations of the described inventive concept, being limited only by the content of the claims, including possible equivalents therein.

The invention claimed is:

1. A system for predicting an association of indisposition to gluten consumption in a user of said system, comprising:
a device configured to capture information related to consumption of a food, such information allowing an identification, estimation and/or association of gluten content of the food;
the device being also configured to receive, through an input interface, information about an individual's food consumption;
a database that receives and stores information related to the food consumption and information on the individual's food consumption, the database also storing a maximum limit for the consumption of gluten admitted for the individual;
a processor to estimate an amount of gluten consumed by the individual from a probabilistic analysis based on information stored in the database and in databases comprising information about the food, forming a history of daily gluten consumption per individual;
wherein the individual, when informing the device, through the input interface, about a physical indisposition, causes the system to carry out evaluation and calculation of a probability of cause of the indisposition to the gluten consumption, in order to predict, by a percentage numerical result, when indisposition to gluten consumption is a result of an immune system's reaction to gluten; and
wherein the evaluation and calculation of the probability of the cause of the indisposition is carried out through:
(a) a first estimate of the probability that symptoms are due to the gluten consumption, based on a statistical analysis based on an initial Poisson cumulative distribution; and
(b) further statistical analysis with adjustments to the Poisson cumulative distribution curve based on data from the user's history, said distribution curve adjustments being performed using artificial intelligence techniques.

2. The system according to claim 1, wherein the system tracks the consumption of gluten most likely to be the cause of indisposition, by evaluating the history of stored consumption data.

\* \* \* \* \*